(12) United States Patent
Raman et al.

(10) Patent No.: US 9,301,918 B2
(45) Date of Patent: *Apr. 5, 2016

(54) ABUSE DETERRENT SOLID DOSAGE FORM FOR IMMEDIATE RELEASE WITH FUNCTIONAL SCORE

(71) Applicant: Mallinckrodt LLC, Hazelwood, MO (US)

(72) Inventors: Siva N. Raman, St. Louis, MO (US); Jae Han Park, Olivette, MO (US); Sunil K. Battu, Manchester, MO (US); Eric A. Burge, Collinsville, IL (US); David W. Bogan, Wentzville, MO (US)

(73) Assignee: MALLINCKRODT LLC, Hazelwood, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/211,307

(22) Filed: Mar. 14, 2014

(65) Prior Publication Data

US 2014/0271849 A1 Sep. 18, 2014

Related U.S. Application Data

(60) Provisional application No. 61/792,951, filed on Mar. 15, 2013.

(51) Int. Cl.
*A61K 9/20* (2006.01)
*A61K 9/46* (2006.01)
*A61K 31/485* (2006.01)
*A61K 47/34* (2006.01)

(52) U.S. Cl.
CPC ............ *A61K 9/0007* (2013.01); *A61K 9/2004* (2013.01); *A61K 9/2031* (2013.01); *A61K 9/2054* (2013.01); *A61K 9/2072* (2013.01); *A61K 31/485* (2013.01); *A61K 47/34* (2013.01)

(58) Field of Classification Search
CPC ..................................................... A61K 9/2004
See application file for complete search history.

(56) References Cited

U.S. PATENT DOCUMENTS

| 2,211,485 | A | 8/1940 | Zimmermann |
| 3,891,756 | A | 6/1975 | Kasugai et al. |
| 3,980,766 | A | 9/1976 | Shaw et al. |
| 4,070,494 | A | 1/1978 | Hoffmeister et al. |

(Continued)

FOREIGN PATENT DOCUMENTS

| EP | 2123274 A1 | 11/2009 |
| JP | 62-089616 | 4/1987 |

(Continued)

OTHER PUBLICATIONS

Usui et al., "Interactions in the Solid State 1: Interactions of Sodium Bicarbonate and Tartaric Acid under Compressed Conditions," J. Pharm. Sci.,1985, pp. 1293-1297, vol. 74, No. 12.

(Continued)

*Primary Examiner* — Carlos Azpuru (57) ABSTRACT

The present disclosure provides an immediate release, abuse deterrent pharmaceutical solid dosage form comprising at least one functional score. In particular, the immediate release, abuse deterrent solid dosage form comprises at least one low molecular weight hydrophilic polymer, at least one high molecular weight hydrophilic polymer, and an effervescent system.

19 Claims, 2 Drawing Sheets

(56) References Cited

U.S. PATENT DOCUMENTS

| | | |
|---|---|---|
| 4,678,661 A | 7/1987 | Gergely et al. |
| 6,071,539 A | 6/2000 | Robinson |
| 6,200,604 B1 | 3/2001 | Pather et al. |
| 6,264,981 B1 | 7/2001 | Zhang et al. |
| 6,309,668 B1 | 10/2001 | Bastin et al. |
| 6,340,471 B1 | 1/2002 | Kershman et al. |
| 6,541,025 B1 | 4/2003 | Kershman et al. |
| 6,713,089 B1 | 3/2004 | Bertelsen et al. |
| 7,201,920 B2 | 4/2007 | Kumar et al. |
| 7,510,726 B2 | 3/2009 | Kumar et al. |
| 7,658,944 B2 | 2/2010 | Holm et al. |
| 7,776,314 B2 | 8/2010 | Bartholomaus et al. |
| 7,955,619 B2 | 6/2011 | Shah et al. |
| 8,075,872 B2 | 12/2011 | Arkenau-Maric et al. |
| 8,114,383 B2 | 2/2012 | Bartholomaus et al. |
| 8,114,384 B2 | 2/2012 | Arkenau et al. |
| 9,078,827 B2 | 7/2015 | Odidi |
| 2003/0068375 A1 | 4/2003 | Wright et al. |
| 2004/0005359 A1 | 1/2004 | Cheng et al. |
| 2005/0165038 A1 | 7/2005 | Gordon |
| 2005/0236741 A1 | 10/2005 | Arkenau et al. |
| 2006/0002860 A1 | 1/2006 | Bartholomaus et al. |
| 2006/0193782 A1 | 8/2006 | Bartholomaus et al. |
| 2007/0004795 A1 | 1/2007 | Sesha |
| 2007/0048228 A1 | 3/2007 | Arkenau-Maric et al. |
| 2007/0183980 A1 | 8/2007 | Arkenau-Maric et al. |
| 2008/0102121 A1 | 5/2008 | Devane |
| 2008/0166405 A1 | 7/2008 | Mehta |
| 2008/0247959 A1 | 10/2008 | Bartholomaus et al. |
| 2008/0248113 A1 | 10/2008 | Bartholomaus et al. |
| 2008/0311187 A1 | 12/2008 | Ashworth et al. |
| 2009/0081290 A1 | 3/2009 | McKenna et al. |
| 2009/0098200 A1 | 4/2009 | Temtsin Krayz et al. |
| 2009/0124650 A1 | 5/2009 | Ahdieh |
| 2009/0175937 A1 | 7/2009 | Rahmouni et al. |
| 2009/0196922 A1 | 8/2009 | Guerrero et al. |
| 2009/0221621 A1 | 9/2009 | Sathyan et al. |
| 2009/0232887 A1 | 9/2009 | Odidi |
| 2009/0317355 A1 | 12/2009 | Roth et al. |
| 2010/0092553 A1 | 4/2010 | Guimberteau et al. |
| 2010/0151028 A1 | 6/2010 | Ashworth et al. |
| 2010/0166858 A1 | 7/2010 | Mehta et al. |
| 2010/0168148 A1 | 7/2010 | Wright et al. |
| 2010/0204259 A1 | 8/2010 | Tygesen et al. |
| 2010/0260833 A1 | 10/2010 | Bartholomaus et al. |
| 2011/0020451 A1 | 1/2011 | Bartholomaus et al. |
| 2011/0054038 A1 | 3/2011 | Glozman |
| 2011/0117196 A1 | 5/2011 | Gordon |
| 2011/0165248 A1 | 7/2011 | Machonis |
| 2011/0268666 A1 | 11/2011 | Friedman et al. |
| 2012/0028937 A1 | 2/2012 | Tsuzuki et al. |
| 2012/0136021 A1 | 5/2012 | Barnscheid et al. |
| 2012/0214777 A1 | 8/2012 | Crowley et al. |
| 2012/0321674 A1 | 12/2012 | Vachon et al. |
| 2012/0321716 A1 | 12/2012 | Vachon et al. |
| 2013/0280176 A1 | 10/2013 | Diezi |
| 2013/0280177 A1 | 10/2013 | Raman |

FOREIGN PATENT DOCUMENTS

| | | |
|---|---|---|
| JP | 2011105615 A | 6/2011 |
| WO | 03/032954 A1 | 4/2003 |
| WO | 2006002836 A1 | 1/2006 |
| WO | 2011/066980 A2 | 6/2011 |
| WO | 2011079074 * | 6/2011 |
| WO | 2011079074 A1 | 6/2011 |
| WO | 2012/112952 A1 | 8/2012 |
| WO | 2013/077851 A1 * | 5/2013 |
| WO | 2013158810 A1 | 10/2013 |
| WO | 2013158814 A1 | 10/2013 |
| WO | 2014152296 A1 | 9/2014 |

OTHER PUBLICATIONS

International Preliminary Report on Patentability dated Oct. 21, 2014 from related International application No. PCT/US2013/037046, 7 pgs.

International Preliminary Report on Patentability dated Oct. 21, 2014 from related International application No. PCT/US2013/037056, 6 pgs.

International Search Report and Written Opinion dated Jul. 10, 2014 from related International application No. PCT/US2014/027176, 10 pgs.

Office action dated Apr. 13, 2015 from related U.S. Appl. No. 13/865,286, 16 pgs.

Office action dated Sep. 15, 2014 from related U.S. Appl. No. 13/865,286, 13 pgs.

Beer Beate, "Impact of slow-release oral morphine on drug abusing habits in Austria", Neuropsychiatrie, Dustri Verlag, Deisenhofen, DE, vol. 24, No. 2, Jan. 1, 2010, pp. 108-117.

Born, Chapter 11 "Xanthan", 2002, pp. 259-269, downloaded from the internet at URL <http://www.wiley-vch.do/books/biopoly/pdf_v09/bpol5011_259_269.pdf>.

Polyox water soluble resins brochure, 2002, 24 pgs., downloaded from the internet from URL <http://msdssearch.dow.com/PublishedLiteratureDOWCOM/dh_0031/0901b80380031a4a.pdf-?filepath=/326-00001.pdf&fromPage=GetDoc>.

Office action issued Oct. 7, 2015 in related U.S. Appl. No. 13/865,244, 9 pgs.

* cited by examiner

ABUSE DETERRENT SOLID DOSAGE FORM FOR IMMEDIATE RELEASE WITH FUNCTIONAL SCORE

CROSS REFERENCE TO RELATED APPLICATIONS

This application claims the benefit of U.S. Provisional Application No. 61/792,951 filed Mar. 15, 2013, which is incorporated herein in its entirety.

FIELD OF THE INVENTION

The present disclosure generally relates to scored solid dosage forms that provide immediate release of active ingredients and have abuse deterrent properties.

BACKGROUND OF THE INVENTION

Abuse of prescription drugs (particularly opioids) is a serious societal problem. Such abuse places an enormous economic burden on society due to increased health care, work place, and criminal justice costs. Attempts have been made to diminish the abuse of opioid solid dosage forms by introducing abuse deterrent features. One approach has been to include in the dosage form an opioid antagonist that is not orally active but will substantially block the analgesic effects of the opioid if one attempts to dissolve the opioid and administer it parenterally. Another approach has been to include gel-forming high molecular weight polymers that make the dosage form difficult to crush and/or pulverize into a powder. These high molecular weight polymers, however, retard the release of the active ingredient from the dosage forms, making them unsuitable for immediate release formulations.

Additionally, having a score (or bisect) on a solid dosage form permits the dosage form to be broken into smaller portions, thus making it possible to evaluate multiple dosing regimens. Incorporating abuse deterrent properties into solid dosage forms (e.g., by increasing the crushing strength), however, may make the dosage forms difficult to break, thereby obviating the functionality of any score. Thus, there is a need for abuse deterrent, immediate release solid dosage forms that are difficult to crush while at the same time have functional scores.

SUMMARY OF THE INVENTION

Among the various aspects of the present disclosure is the provision of a pharmaceutical solid dosage form comprising at least one active pharmaceutical ingredient (API) or a pharmaceutically acceptable salt thereof, at least one low molecular weight hydrophilic polymer, at least one high molecular weight hydrophilic polymer, and an effervescent system, wherein the solid dosage form comprises at least one score.

Other aspects and iterations of the disclosure are described in more detail below.

DETAILED DESCRIPTION OF THE INVENTION

The present disclosure provides immediate release pharmaceutical solid dosage forms having abuse deterrent properties which also comprise at least one score. The score permits splitting of the solid dosage form when less than a full dose of the solid dosage form is desired. The score is functional when the solid dosage form can be split into equal parts with minimal loss of mass, and wherein the split parts contain equal amounts of the active ingredient and retain the immediate release and abuse deterrent features of the intact solid dosage form. Also provided are processes for preparing the scored, immediate release, abuse deterrent solid dosage forms.

(I) Pharmaceutical Solid Dosage Forms

One aspect of the present disclosure provides pharmaceutical solid dosage forms having immediate release and abuse deterrent properties that also comprise at least one score. Detailed below are properties of the scored solid dosage forms and portions thereof, components of the solid dosage forms, release characteristics of the solid dosage forms, and abuse deterrent properties of the solid dosage forms.

(a) Scores

The shape of the solid dosage form comprising at least one score may vary. For example, the solid dosage form may have, without limit, a substantially oval, ellipsoid, rectangular, discoid, circular, square, triangular, or hexagonal shape. The shape of the solid dosage form is such that the solid dosage form comprises an upper surface and a lower surface. The upper and/or lower surfaces may be substantially flat (planar). Alternatively, the upper and/or lower surfaces may be convex in that the central portion of the surface is raised relative to the peripheral edges of the surface. In some embodiments, the solid dosage form may comprise a circumferential (belly) band. Non-limiting examples of suitable solid dosage units include tablets, caplets, and pills. In exemplary embodiments, the solid dosage form is a tablet. The tablet may be, without limit, compressed, compacted, molded, pressed, monolithic, layered, multiparticle, extruded, uncoated, or coated.

Figure 1:
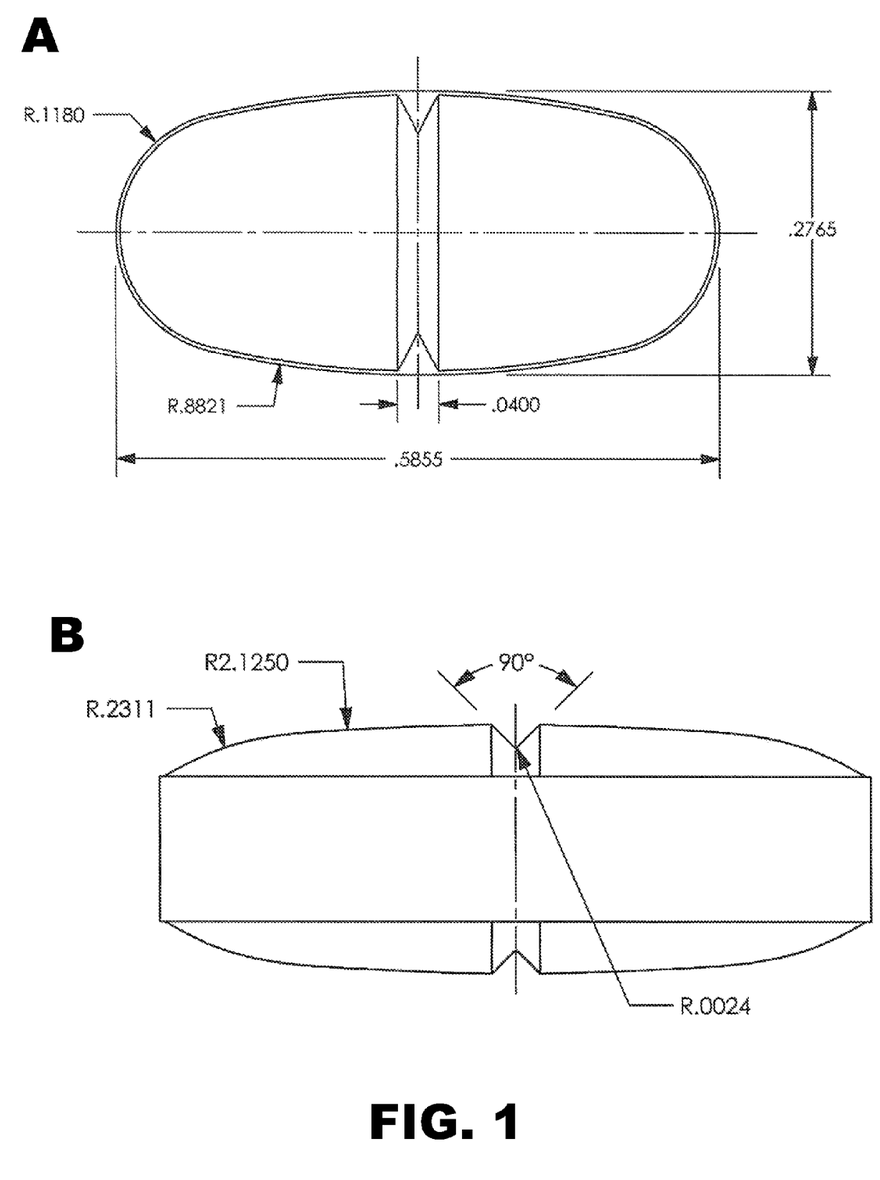
FIG. 1 presents views of an oval tablet with E type scores. (A) shows a face view and (B) presents a side view.

The type of score on the solid dosage form may vary. For example, the score may be a standard score (E type; see FIG. 1), a decreasing score (C type; see FIG. 2), a standard protruding score (A type), a pressure sensitive score (G type), a cut through score (D type), a short score (B type), or a partial score (H type). The shape of the score may vary. For instance, the score may be a V-shaped groove, a U-shaped groove, combinations, or variations thereof. The inner angle of the groove may range from about 30° to about 150°. In one embodiment, the groove may have a V-shape with an inner angle of about 90°. The depth of the groove may also vary. In various embodiments, the depth of the groove may range from about 2% to about 30% of the total thickness of the solid dosage form.

In some embodiments, the solid dosage form may comprise one score, with the score being located on either the upper surface or the lower surface of the dosage form. Alternatively, the solid dosage form may comprise a first score on the upper surface and a second score on the lower surface (see FIG. 1B). In embodiments in which the solid dosage form comprises a single score on either one or both of the surfaces, the score is centrally located such that splitting the scored solid dosage form yields two equal-sized solid dosage portions (or halves). Generally, the score is parallel to the shortest axis of the solid dosage form.

In other embodiments, the solid dosage form may comprise two or more scores on the upper and/or lower surfaces. For example, one or both of the surfaces may comprise two, three, four, five, six, seven, or more scores. In cases where the solid dosage form comprises two parallel scores on one or both of the surfaces, splitting the scored solid dosage form yields three equal-sized solid dosage portions (or thirds). In instances where the solid dosage form comprises two intersecting sores or three parallel scores on one or both of the surfaces, splitting the scored solid dosage form yields four equal-sized solid dosage portions (or quarters).

In general, the score of the solid dosage form is a functional score. A score is functional if the solid dosage form can be split manually (i.e., by hand) or mechanically (i.e., using a tablet splitter) into equal-sized solid dosage portions, with minimal loss of mass. The split solid dosage portions have similar weights and similar contents (i.e., each split solid dosage portion has an equivalent fraction of the active ingredient present in the intact solid dosage form). For example, the relative standard deviation (RSD) of the average weight of the split solid dosage portions may be less than about 5%. In general, the loss of mass upon splitting is less than 3.0%. In some embodiments, the loss of mass upon splitting is less than about 2.8%, 2.6%, 2.4%, 2.2%, 2.0%, 1.8%, 1.6%, 1.4%, 1.2%, 1.0%, 0.8%, 0.6%, 0.4%, 0.2%, 0.1%, 0.08%, 0.06%, 0.04%, 0.02%, or 0.01%. The split solid dosage portions generally have a friability of less than about 1%. In various embodiments, the split solid dosage portions may have a friability of less than about 0.9%, 0.8%, 0.7%, 0.6%, 0.5%, 0.4%, 0.3%, 0.2%, 0.1%, 0.08%, 0.06%, 0.04%, 0.02%, 0.01%, 0.005%, or 0.001%.

The split solid dosage portions also exhibit the same dissolution profiles and abuse deterrent properties as the intact solid dosage form. In vitro dissolution may be measured as detailed below in section (I)(c). In some embodiments, the split solid dosage portions may have an average release of about 50%, 55%, 60%, 65%, 70%, 75%, 80%, 85%, 90%, 95%, or 99% of the API within 45 minutes in water. In other embodiments, the split solid dosage portions may have an average release of about 50%, 55%, 60%, 65%, 70%, 75%, 80%, 85%, 90%, 95%, or 99% of the API within 30 minutes in water.

Similar to the intact solid dosage form, the split solid dosage portions deter inhalation abuse because they are resistant to crushing, grinding, or pulverizing to form a powder comprising small particles. Means for determining resistance to crushing, grinding, or pulverizing are detailed below in section (I)(d). In embodiments in which the split solid dosage portions are subjected to 6 minutes of milling in a high shear mill to form particles, more than 20%, 30%, 40%, 50%, 60%, 70%, 80%, 90%, or 95% of the particles have an average diameter of at least about 250 microns.

Similarly, the split solid dosage portions also are resistant to abuse by extraction or injection because the split solid dosage portions or fragments thereof form viscous mixtures or gels when in contact with small volumes of suitable solvents, as detailed below in section (I)(d).

(b) Components

The pharmaceutical solid dosage forms disclosed herein comprise at least one low molecular weight hydrophilic polymer, at least one high molecular weight hydrophilic polymer, and an effervescent system. The combination of hydrophilic polymers of different molecular sizes and the effervescent system yields a functional abuse deterrent, immediate release pharmaceutical solid dosage form.

(i) Hydrophilic Polymers

The pharmaceutical solid dosage forms disclosed herein comprise hydrophilic polymers of different molecular weights. The term "hydrophilic polymer" refers to a polymer with affinity for water such that it readily absorbs and/or dissolves in water or an aqueous solution. Hydrophilic polymers may be soluble in water or an aqueous solution and/or swellable in water or an aqueous solution. Polymers that swell in water or an aqueous solution may be termed gelling polymers.

A variety of hydrophilic polymers are suitable for use in the pharmaceutical solid dosage forms. The hydrophilic polymer may be natural, semi-synthetic, or synthetic. In some embodiments, the hydrophilic polymer may be a polyalkylene oxide such as polyethylene oxide (PEO), polypropylene oxide, combinations thereof, or copolymers thereof. In other embodiments, the hydrophilic polymer may be a cellulose ether, which is a cellulose derivative in which the hydrogen atoms of hydroxyl groups are replaced with alkyl groups. Non-limiting examples of suitable cellulose ethers include hydroxypropyl cellulose (HPC), hydroxypropyl methylcellulose (HPMC), carboxymethylcellulose (CMC), methylcellulose, hydroxyethyl cellulose, hydroxyethyl methylcellulose, and the like. In still other embodiments, the hydrophilic polymer may be a polyalkylene glycol such as polyethylene glycol (PEG) (e.g., PEG 1000, PEG 2000, PEG 3300, PEG 4000, PEG 5000, PEG 6000, PEG 8000, PEG 10,000, PEG 20,000, PEG 30,000), derivatives thereof, combinations thereof, and copolymers thereof. In further embodiments, the hydrophilic polymer may be a Poloxamer, which is a Bifunctional, triblock copolymer of ethylene oxide and polyproplylene oxide (available under the tradenames KOLLIPHOR™ or PLURONIC®). Available Poloxamers include Poloxamers 101, 105, 108, 122, 123, 124, 181, 182, 183, 184, 185, 188, 212, 215, 217, 231, 234, 235, 237, 238, 282, 284, 288, 331, 333, 334, 335, 338, 401, 402, 403, and 407, wherein the first two digits multiplied by 100 give the approximate molecular mass and the last digit multiplied by 10 gives the percentage of the polyoxyethylene oxide content. In one embodiment, the hydrophilic polymer may be Poloxamer 407. In still other embodiments, the hydrophilic polymer may be a polysaccharide. Suitable polysaccharides include, without limit, celluloses, starches, pectins, chitins, gums (i.e., polysaccharides derived from plants or microbes), combinations thereof, and derivatives thereof. Non-limiting examples of suitable gums include xanthan gum, acacia gum, diutan gum, gellan gum, guar gum, fenugreek gum, locust bean gum, pullulan, welan gum, or combinations thereof. In additional embodiments, the hydrophilic polymer may be a polycarboxylic acid such as polyacrylic acid, polyacrylic acid-co-acrylamide, polymethacrylate, polyhydroxyethyl methacrylate, combinations, or copolymers thereof. In other embodiments, the hydrophilic polymer may be a polyamine such as polyethyleneimine, polyvinylamine, or the like. In further embodiments, the hydrophilic polymer may be a polypeptide such as gelatin, albumin, polylysine, soy protein, and so forth. In still further embodiments, the hydrophilic polymer may be a polyolefinic alcohol (such as polyvinyl alcohol), or a polyvinyl lactam (such as, e.g., polyvinylpyrrolidone, polyvinyl caprolactam, and the like). The hydrophilic polymer also may be a combination or a copolymer of any of the foregoing.

(ii) Low Molecular Weight Hydrophilic Polymer

The pharmaceutical solid dosage forms comprise at least one low molecular weight hydrophilic polymer. As used herein, the term "low molecular weight polymer" refers to a polymer having an average molecular weight of no more than about 250,000 Da. In various embodiments, the average molecular weight of a low molecular weight polymer may range from about 250,000 to about 200,000 Da, from about 200,000 to about 150,000 Da, from about 150,000 to about 125,000 Da, from about 125,000 to about 100,000 Da, from about 100,000 to about 75,000 Da, from about 75,000 to about 50,000 Da, from about 50,000 to about 25,000 Da, or from about 25,000 to about 1000 Da. In some embodiments, the pharmaceutical solid dosage form may comprise a hydrophilic polymer having an average molecular weight of no more than about 250,000 Da. In other embodiments, the pharmaceutical solid dosage form may comprise a hydrophilic polymer having an average molecular weight of about 250,000 Da or less. In further embodiments, the pharmaceutical solid dosage form may comprise a hydrophilic polymer having an average molecular weight of about 100,000 Da or less. In still other embodiments, the pharmaceutical solid dosage form may comprise a hydrophilic polymer having an average molecular weight of about 30,000 Da or less.

In one embodiment, the pharmaceutical solid dosage form comprises one hydrophilic polymer having an average molecular weight of no more than about 250,000 Da. In another embodiment, the pharmaceutical solid dosage form comprises two hydrophilic polymers, the average molecular weight of each being no more than about 250,000 Da. In still another embodiment, the pharmaceutical solid dosage form comprises three hydrophilic polymers, the average molecular weight of each being no more than about 250,000 Da. In a further embodiment, the pharmaceutical solid dosage form comprises four hydrophilic polymers, the average molecular weight of each being no more than about 250,000 Da. In yet another embodiment, the pharmaceutical solid dosage form comprises five hydrophilic polymers, the average molecular weight of each being no more than about 250,000 Da. Examples of suitable hydrophilic polymers are detailed above in section (I)(a)(i).

In one embodiment, the pharmaceutical solid dosage form comprises polyethylene oxide having an average molecular weight of about 100,000 Da, or an average molecular weight of about 200,000 Da. In another embodiment, the pharmaceutical solid dosage form comprises hydroxypropyl methylcellulose having an average molecular weight of about 100,000 Da, about 150,000, or ranging from about 200,000 to about 220,000 Da. In still another embodiment, the pharmaceutical solid dosage form comprises (sodium) carboxymethylcellulose having an average molecular weight of about 30,000 Da, or an average molecular weight of about 90,000 Da. In a further embodiment, the pharmaceutical solid dosage form comprises polyethylene glycol having an average molecular weight of about 3,300 Da, about 5,000 Da, or about 10,000 Da. In yet another embodiment, the pharmaceutical solid dosage form comprises a Poloxamer having an average molecular weight of about 10,000 Da or less.

The amount of the low molecular weight hydrophilic polymer present in the pharmaceutical solid dosage form can and will vary depending upon the desired properties of the pharmaceutical composition, as well as the identity and amounts of other components present in the dosage form. In general, the amount of the low molecular weight hydrophilic polymer present may range from about 5% to about 50% by weight of the pharmaceutical solid dosage form. In various embodiments, the amount of the low molecular weight hydrophilic polymer may range from about 5% to about 10%, from about 10% to about 15%, from about 15% to about 20%, from about 20% to about 25%, from about 25% to about 30%, from about 30% to about 40%, or from about 40% to about 50% by weight of the pharmaceutical solid dosage form. In one embodiment, the amount of the low molecular weight polymer present may range from about 15% to about 45% by weight of the pharmaceutical solid dosage form. In an exemplary embodiment, the amount of the low molecular weight polymer present may range from about 20% to about 40% by weight of the pharmaceutical solid dosage form.

(iii) High Molecular Weight Hydrophilic Polymer

The pharmaceutical solid dosage form disclosed herein also comprises at least one high molecular weight hydrophilic polymer. A "high molecular weight polymer," as used herein, refers to a polymer having an average molecular weight of at least about 400,000 Da. In general, the average molecular weight of the high molecular weight polymer may range from about 400,000 to about 15,000,000 Da. For example, the high molecular weight polymer may have an average molecular weight that ranges from about 400,000 to about 600,000 Da, from about 600,000 to about 800,000 Da, from about 800,000 to 1,000,000 Da, from about 1,000,000 to about 4,000,000 Da, from about 4,000,000 to about 8,000,000 Da, from about 8,000,000 to about 12,000,000 Da, or from about 12,000,000 to about 15,000,000 Da. In some embodiments, the pharmaceutical solid dosage form may comprise a hydrophilic polymer having an average molecular weight of at least about 4,000,000 Da. In other embodiments, the pharmaceutical solid dosage form may comprise a hydrophilic polymer having an average molecular weight of at least about 1,000,000 Da. In further embodiments, the pharmaceutical solid dosage form may comprise a hydrophilic polymer having an average molecular weight of at least about 800,000 Da.

In one embodiment, the pharmaceutical solid dosage form comprises one hydrophilic polymer having an average molecular weight of at least about 400,000 Da. In another embodiment, the pharmaceutical solid dosage form comprises two hydrophilic polymers, the average molecular weight of each being at least about 400,000 Da. In still another embodiment, the pharmaceutical solid dosage form comprises three hydrophilic polymers, the average molecular weight of each being at least about 400,000 Da. In a further embodiment, the pharmaceutical solid dosage form comprises four hydrophilic polymers, the average molecular weight of each being at least about 400,000 Da. Examples of suitable hydrophilic polymers are detailed above in section (I)(a)(i).

In one embodiment, the pharmaceutical solid dosage form comprises polyethylene oxide having an average molecular weight of at least about 1,000,000 Da. In another embodiment, the pharmaceutical solid dosage form comprises polyethylene oxide having an average molecular weight of about 4,000,000 Da. In a further embodiment, the pharmaceutical solid dosage form comprises xanthan gum having an average molecular weight of at least about 1,000,000 Da. In still another embodiment, the pharmaceutical solid dosage form comprises hydroxypropyl cellulose having an average molecular weight of at least about 800,000 Da.

The amount of the high molecular weight hydrophilic polymer present in the pharmaceutical solid dosage form can and will vary depending upon the desired properties of the pharmaceutical composition, as well as the identity and amounts of other components present in the composition. In general, the amount of the high molecular weight polymer present may range from about 0.1% to about 30% by weight of the pharmaceutical solid dosage form. In various embodiments, the amount of the high molecular weight polymer present may range from about 0.1% to about 0.3%, from about 0.3% to about 1%, from about 1% to about 3%, from about 3% to about 10%, or from about 10% to about 30% by weight of the pharmaceutical solid dosage form. In one embodiment, the amount of the high molecular weight hydrophilic polymer present may range from about 1% to about 15% by weight of the pharmaceutical solid dosage form. In an exemplary embodiment, the amount of the high molecular weight hydrophilic polymer present may range from about 2% to about 10% by weight of the pharmaceutical solid dosage form.

(iv) Effervescent System

The pharmaceutical solid dosage forms disclosed herein also comprise an effervescent system. As used herein, an "effervescent system" refers to a system generally comprising an acid component and a base component, wherein the system liberates carbon dioxide upon contact with an aqueous solution. Without being bound by any particular theory, it is believed that the effervescent system facilitates rapid dissolution of the API from a composition comprising the combination of low and high molecular weight hydrophilic polymers.

The acid component of the effervescent system may be an organic acid, an inorganic acid, or a combination thereof. Non-limiting examples of suitable acids include adipic acid, ascorbic acid, benzoic acid, citric acid, fumaric acid, glutaric acid, lactic acid, lauric acid, malic acid, maleic acid, malonic acid, oxalic acid, phthalic acid, sorbic acid, succinic acid, tartaric acid, ammonium phosphate, potassium bitartrate, potassium phosphate, dipotassium phosphate, disodium pyrophosphate, sodium acid pyrophosphate, sodium phosphate, disodium phosphate, and combinations thereof. In exemplary embodiments, the acid component of the effervescent system may be an organic acid. In one exemplary embodiment, the acid component may be tartaric acid. In other embodiments, the acid component of the effervescent system may be an inorganic acid.

In some embodiments, the acid component of the effervescent system may be co-processed with a polyalkylene glycol or a Poloxamer. Suitable polyalkylene glycols and Poloxamers are detailed above in section (I)(a)(i). The acid and the polyalkylene glycol/Poloxamer may be co-processed by a variety of means including, without limit, hot melt granulation, fluidized hot melt granulation, hot melt mixing, wet granulation, liquid spray mixing, and the like. The amount of polyalkylene glycol/Poloxamer co-processed with the acid can and will vary. In general, the weight to weight ratio of the acid to the polyalkylene glycol/Poloxamer may range from about 1:0.01 to about 1:0.5.

The base component of the effervescent system may be a bicarbonate, a carbonate, or a combination thereof. In various embodiments, the base may be an alkali metal bicarbonate, an alkaline earth metal bicarbonate, an alkali metal carbonate, an organic carbonate, or combinations thereof. Non-limiting examples of suitable bases include ammonium bicarbonate, calcium bicarbonate, lithium bicarbonate, magnesium bicarbonate, potassium bicarbonate, sodium bicarbonate, arginine carbonate, ammonium carbonate, calcium carbonate, lysine carbonate, potassium magnesium carbonate, sodium carbonate, sodium glycine carbonate, sodium sesquicarbonate, zinc carbonate, and combinations thereof. In exemplary embodiments, the base may be an alkali metal bicarbonate. In one exemplary embodiment, the base may be sodium bicarbonate. In another exemplary embodiment, the base may be heat-treated sodium bicarbonate (for example EfferSoda®12).

The mole to mole ratio of the acid component to the base component in the effervescent system may also vary depending, for example, upon the identity of the acid and the base. In general, the mole to mole ratio of the acid component to the base component in the effervescent system may range from about 1:0.2 to about 1:5. For example, the mole to mole ratio of the acid component to the base component in the effervescent system may be about 1:0.2, about 1:0.25, about 1:0.33, about 1:0.5, about 1:1, about 1:2, about 1:3, about 1:4, about 1:5 or any ratio in between. In one exemplary embodiment, the mole to mole ratio of the acid component to the base component in the effervescent system may range from about 1:1 to about 1:3. In another exemplary embodiment, the mole to mole ratio of the acid component to the base component in the effervescent system may be about 1:2.

The amount of the effervescent system present in the pharmaceutical solid dosage form can and will vary depending upon the identity of the other components and the desired properties of the pharmaceutical composition. In general, the amount of the effervescent system present may range from about 20% to about 90% by weight of the pharmaceutical solid dosage form. In various embodiments, the amount of the effervescent system present may be from about 20% to about 30%, from about 30% to about 40%, from about 40% to about 50%, from about 50% to about 60%, from about 60% to about 70%, from about 70% to about 80%, or from about 80% to about 90% by weight of the pharmaceutical solid dosage form. In certain embodiments, the amount of the effervescent system present may range from about 40% to about 80% by weight of the pharmaceutical solid dosage form. In one exemplary embodiment, the amount of the effervescent system present may range from about 50% to about 70% by weight of the pharmaceutical solid dosage form.

(v) API

The pharmaceutical solid dosage form disclosed herein comprises at least one API or salt thereof. Suitable APIs include, without limit, opioid analgesic agents (e.g., adulmine, alfentanil, allocryptopine, allylprodine, alphaprodine, anileridine, aporphine, benzylmorphine, berberine, bicuculine, bicucine, bezitramide, buprenorphine, bulbocaprine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papavereturn, pentazocine, phenadoxone, phenomorphan, phenazocine, phenoperidine, piminodine, piritramide, propheptazine, promedol, properidine, propoxyphene, sufentanil, tapentadol, tilidine, and tramadol); non-opioid analgesic agents (e.g., acetylsalicylic acid, acetaminophen, paracetamol, ibuprofen, ketoprofen, indomethacin, diflunisol, naproxen, ketorolac, dichlophenac, tolmetin, sulindac, phenacetin, piroxicam, and mefamanic acid); anti-inflammatory agents (e.g., glucocorticoids such as alclometasone, fluocinonide, methylprednisolone, triamcinolone and dexamethasone; non-steroidal anti-inflammatory agents such as celecoxib, deracoxib, ketoprofen, lumiracoxib, meloxicam, parecoxib, rofecoxib, and valdecoxib); antitussive agents (e.g., dextromethorphan, codeine, hydrocodone, caramiphen, carbetapentane, and dextromethorphan); antipyretic agents (e.g., acetylsalicylic acid and acetaminophen); antibiotic agents (e.g., aminoglycosides such as, amikacin, gentamicin, kanamycin, neomycin, netilmicin, streptomycin, and tobramycin; carbecephern such as loracarbef; carbapenems such as certapenem, imipenem, and meropenem; cephalosporins such as cefadroxil cefazolin, cephalexin, cefaclor, cefamandole, cephalexin, cefoxitin, cefprozil, cefuroxime, cefixime, cefdinir, cefditoren, cefoperazone, cefotaxime, cefpodoxime, ceftazidime, ceftibuten, ceftizoxime, and ceftriaxone; macrolides such as azithromycin, clarithromycin, dirithromycin, erythromycin, and troleandomycin; monobactam; penicillins such as amoxicillin, ampicillin, carbenicillin, cloxacillin, dicloxacillin, nafcillin, oxacillin, penicillin G, penicillin V, piperacillin, and ticarcillin; polypeptides such as bacitracin, colistin, and polymyxin B; quinolones such as ciprofloxacin, enoxacin, gatifloxacin, levofloxacin, lomefloxacin, moxifloxacin, norfloxacin, ofloxacin, and trovafioxacin; sulfonamides such as mafenide, sulfacetamide, sulfamethizole, sulfasalazine, sulfisoxazole, and trimethoprim-sulfamethoxazole; tetracyclines such as demeclocycline, doxycycline, minocycline, and oxytetracycline); antimicrobial agents (e.g., ketoconazole, amoxicillin, cephalexin, miconazole, econazole, acyclovir, and nelfinavir); antiviral agents (e.g., acyclovir, gangciclovir, oseltamivir, and relenza); steroids (e.g., estradiol, testosterone, cortisol, aldosterone, prednisone, and cortisone); amphetamine stimulant agents (e.g., amphetamine and amphetamine-like drugs); non-amphetamine stimulant agents (e.g., methylphenidate, nicotine, and caffeine); laxative agents (e.g., bisacodyl, casanthranol, senna, and castor oil); anti-nausea agents (e.g., dolasetron, granisetron, ondansetron, tropisetron, meclizine, and cyclizine); anorexic agents (e.g., fenfluramine, dexfenfluramine, mazindol, phentermine, and aminorex); antihistaminic agents (e.g., phencarol, cetirizine, cinnarizine, ethamidindole, azatadine, brompheniramine, hydroxyzine, and chlorpheniramine); antiasthmatic agents (e.g., zileuton, montelukast, omalizumab, fluticasone, and zafirlukast); antidiuretic agents (e.g., desmopressin, vasopressin, and lypressin); antimigraine agents (e.g., naratriptan, frovatriptan, eletriptan, dihydroergotamine, zolmitriptan, almotriptan, and sumatriptan); antispasmodic agents (e.g., dicyclomine, hyoscyamine, and peppermint oil); antidiabetic agents (e.g., methformin, acarbose, miglitol, pioglitazone, rosiglitazone, nateglinide, repaglinide, mitiglinide, saxagliptin, sitagliptine, vildagliptin, acetohexamide, chlorpropamide, gliclazide, glimepiride, glipizide, glyburide, tolazamide, and tolbutamide); respiratory agents (e.g., albuterol, ephedrine, metaproterenol, and terbutaline); sympathomimetic agents (e.g., pseudoephedrine, phenylephrine, phenylpropanolamine, epinephrine, norepinephrine, dopamine, and ephedrine); H2 blocking agents (e.g., cimetidine, famotidine, nizatidine, and ranitidine); antihyperlipidemic agents (e.g., clofibrate, cholestyramine, colestipol, fluvastatin, atorvastatin, genfibrozil, lovastatin, niacin, pravastatin, fenofibrate, colesevelam, and simvastatin); antihypercholesterol agents (e.g., lovastatin, simvastatin, pravastatin, fluvastatin, atorvastatin, cholestyramine, colestipol, colesevelam, nicotinic acid, gemfibrozil, and ezetimibe); cardiotonic agents (e.g., digitalis, ubidecarenone, and dopamine); vasodilating agents (e.g., nitroglycerin, captopril, dihydralazine, diltiazem, and isosorbide dinitrate); vasoconstricting agents (e.g., dihydroergotoxine and dihydroergotamine); anticoagulants (e.g., warfarin, heparin, and Factor Xa inhibitors); sedative agents (e.g., amobarbital, pentobarbital, secobarbital, clomethiazole, diphenhydramine hydrochloride, and alprazolam); hypnotic agents (e.g., zaleplon, zolpidem, eszopiclone, zopiclone, chloral hydrate, and clomethiazole); anticonvulsant agents (e.g., lamitrogene, oxycarbamezine, phenyloin, mephenyloin, ethosuximide, methsuccimide, carbamazepine, valproic acid, gabapentin, topiramate, felbamate, and phenobarbital); muscle relaxing agents (e.g., baclofen, carisoprodol, chlorzoxazone, cyclobenzaprine, dantrolene sodium, metaxalone, orphenadrine, pancuronium bromide, and tizanidine); antipsychotic agents (e.g., phenothiazine, chlorpromazine, fluphenazine, perphenazine, prochlorperazine, thioridazine, trifluoperazine, haloperidol, droperidol, pimozide, clozapine, olanzapine, risperidone, quetiapine, ziprasidone, melperone, and paliperidone); antianxiolitic agents (e.g., lorazepam, alprazolam, clonazepam, diazepam, buspirone, meprobamate, and flunitrazepam); antihyperactive agents (e.g., methylphenidate, amphetamine, and dextroamphetamine); antihypertensive agents (e.g., alpha-methyldopa, chlortalidone, reserpine, syrosingopine, rescinnamine, prazosin, phentolamine, felodipine, propanolol, pindolol, labetalol, clonidine, captopril, enalapril, and lisonopril); antineoplasia agents (e.g., taxol, actinomycin, bleomycin A2, mitomycin C, daunorubicin, doxorubicin, epirubicin, idarubicin, and mitoxantrone); soporific agents (e.g., zolpidem tartrate, eszopiclone, ramelteon, and zaleplon); tranquilizer agents (e.g., alprazolam, clonazepam, diazepam, flunitrazepam, lorazepam, triazolam, chlorpromazine, fluphenazine, haloperidol, loxapine succinate, perphenazine, prochlorperazine, thiothixene, and trifluoperazine); decongestant agents (e.g., ephedrine, phenylephrine, naphazoline, and tetrahydrozoline); beta blockers (e.g., levobunolol, pindolol, timolol maleate, bisoprolol, carvedilol, and butoxamine); alpha blockers (e.g., doxazosin, prazosin, phenoxybenzamine, phentolamine, tamsulosin, alfuzosin, and terazosin); non-steroidal hormones (e.g., corticotropin, vasopressin, oxytocin, insulin, oxendolone, thyroid hormone, and adrenal hormone); erectile disfunction improvement agents; herbal agents (e.g., glycyrrhiza, aloe, garlic, nigella sativa, rauwolfia, St John's wort, and valerian); enzymes (e.g., lipase, protease, amylase, lactase, lysozyme, and urokinase); humoral agents (e.g., prostaglandins, natural and synthetic, for example, PGE1, PGE2alpha, PGF2alpha, and the PGE1 analog misoprostol); psychic energizers (e.g., 3-(2-aminopropy) indole and 3-(2-aminobutyl)indole); nutritional agents; essential fatty acids; non-essential fatty acids; vitamins; minerals; and combinations thereof.

Any of the above-mentioned APIs may be incorporated in the pharmaceutical solid dosage form described herein in any suitable form, such as, for example, as a pharmaceutically acceptable salt, uncharged or charged molecule, molecular complex, solvate or hydrate, prodrug, and, if relevant, isomer, enantiomer, racemic mixture, and/or mixtures thereof. Furthermore, the API may be in any of its crystalline, semi-crystalline, amorphous, or polymorphous forms.

In one embodiment, the API present in the pharmaceutical solid dosage form may have a potential for abuse. For example, the API may be an opioid analgesic agent, a stimulant agent, a sedative agent, a hypnotic agent, an antianxiolitic agent, or a muscle relaxing agent.

In another embodiment, the API present in the pharmaceutical solid dosage form may be a combination of an opioid analgesic and a non-opioid analgesic. Suitable opioid and non-opioid analgesics are listed above.

In a preferred embodiment, the API in the pharmaceutical solid dosage form may be an opioid analgesic. Exemplary opioid analgesics include oxycodone, oxymorphone, hydrocodone, hydromorphone, codeine, and morphine. In one exemplary embodiment, the API may be oxycodone hydrochloride. In another exemplary embodiment, the API may be oxymorphone hydrochloride.

The amount of the API in the pharmaceutical solid dosage form can and will vary depending upon the active agent. In embodiments in which the API is an opioid analgesic, the amount of opioid in the pharmaceutical solid dosage form may range from about 2 mg to about 160 mg. In various embodiments, the amount of opioid in the pharmaceutical solid dosage form may range from about 2 mg to about 10 mg, from about 10 mg to about 40 mg, from about 40 mg to about 80 mg, or from about 80 mg to about 160 mg. In certain embodiments, the amount of opioid in the pharmaceutical solid dosage form may be about 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 45 mg, 50 mg, 60 mg, 70 mg, 80 mg, 100 mg, 120 mg, 140 mg, or 160 mg.

In embodiments in which the opioid is oxycodone hydrochloride, the total amount of oxycodone hydrochloride present in the pharmaceutical solid dosage form may range from about 2 mg to about 80 mg. In certain embodiments, the amount of oxycodone hydrochloride in the pharmaceutical solid dosage form may range from about 2 mg to about 10 mg, from about 10 mg to about 30 mg, or from about 30 mg to about 80 mg. In exemplary embodiments, the amount of oxycodone hydrochloride present in the pharmaceutical solid dosage form may be about 5 mg, about 10 mg, about 15 mg, about 20 mg, about 30 mg, about 40 mg, about 60 mg, or about 80 mg.

In embodiments in which the opioid is oxymorphone hydrochloride, the total amount of oxymorphone hydrochloride present in the pharmaceutical solid dosage form may range from about 2 mg to about 80 mg. In certain embodiments, the amount of oxymorphone hydrochloride present in the pharmaceutical solid dosage form may range from about 2 mg to about 10 mg, from about 10 mg to about 30 mg, or from about 30 mg to about 80 mg. In preferred embodiments, the amount of oxymorphone hydrochloride present in the pharmaceutical solid dosage form may be about 5 mg, about 10 mg, about 20 mg, about 30 mg, or about 40 mg.

(iv) Lubricant

The pharmaceutical solid dosage form disclosed herein may also comprise a lubricant. Non-limiting examples of suitable lubricants include metal stearate such as magnesium stearate, calcium stearate, zinc stearate, colloidal silicon dioxide, hydrogenated vegetable oils, sterotex, polyoxyethylene monostearate, polyethylene glycol, sodium stearyl fumarate, sodium benzoate, sodium lauryl sulfate, magnesium lauryl sulfate, light mineral oil, and combinations thereof. In exemplary embodiments, the lubricant may be a metal stearate. In one exemplary embodiment, the lubricant may be magnesium stearate.

The amount of lubricant present in the pharmaceutical solid dosage form can and will vary depending upon the identities and amounts of other components in the pharmaceutical composition. In general, the amount of lubricant present may range from about 0.1% to about 3% by weight of the pharmaceutical solid dosage form. In various embodiments, the amount of lubricant present may range from about 0.1% to about 0.3%, from about 0.3 to about 1%, or from about 1% to about 3% by weight of the pharmaceutical solid dosage form. In exemplary embodiments, the amount of lubricant present may range from about 0.0.1% to about 2% by weight of the pharmaceutical solid dosage form. In one exemplary embodiment, the amount of lubricant present may range from about 0.3% to about 1% by weight of the pharmaceutical solid dosage form.

(vii) Optional Excipients

In various embodiments, the pharmaceutical solid dosage forms disclosed herein may further comprise at least one additional pharmaceutically acceptable excipient. Non-limiting examples of suitable excipients include clay minerals, binders, fillers, diluents, antioxidants, chelating agents, flavoring agents, coloring agents, taste masking agents, and combinations thereof.

In one embodiment, the excipient may be a clay mineral. A clay mineral refers to a hydrated aluminum phyllosilicate or a hydrated magnesium silicate comprising small insoluble particles. Mixing a clay mineral with a suitable solvent forms a colloidal dispersion of small particles that do not sediment. Non-limiting examples of suitable clay minerals include talc, bentonites, kaolinites, nontronites, montmorillonites, pyrophyllites, saponites, sauconites, vermiculites, and combinations thereof. In one iteration, the clay mineral may be powdered talc or micronized talc.

In a further embodiment, the excipient may be a binder. Suitable binders include, but are not limited to, starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, peptides, and combinations thereof.

In another embodiment, the excipient may be a filler. Suitable fillers include carbohydrates, inorganic compounds, and polyvinylpyrrolidone. In various embodiments, the filler may be calcium sulfate, calcium phosphate, calcium silicate, microcrystalline cellulose, starch, modified starches, lactose, sucrose, mannitol, sorbitol, or combinations thereof.

In another embodiment, the excipient may include a diluent. Non-limiting examples of diluents suitable for use include pharmaceutically acceptable saccharides such as sucrose, dextrose, lactose, microcrystalline cellulose, fructose, xylitol, and sorbitol; polyhydric alcohols; starches; pre-manufactured direct compression diluents; and mixtures of any of the foregoing.

In yet another embodiment, the excipient may be an antioxidant. Suitable antioxidants include, without limit, ascorbyl palmitate, butylated hydroxyanisole, a mixture of 2 and 3 tertiary-butyl-4-hydroxyanisole, butylated hydroxytoluene, sodium isoascorbate, dihydroguaretic acid, potassium sorbate, sodium bisulfate, sodium metabisulfate, sorbic acid, potassium ascorbate, vitamin E, 4-chloro-2,6-ditertiarybutylphenol, alphatocopherol, and propylgallate.

In an alternate embodiment, the excipient may be a chelating agent. Non-limiting examples of suitable chelating agents include ethylenediamine tetracetic acid (EDTA) and its salts, N-(hydroxy-ethyl)ethylenediaminetriacetic acid, nitrilotriacetic acid (NIA), ethylene-bis(oxyethylene-nitrilo)tetraacetic acid, 1,4,7,10-tetraazacyclodo-decane-N,N',N'',N'''-tetraacetic acid, 1,4,7,10-tetraaza-cyclododecane-N,N',N''-triacetic acid, 1,4,7-tris(carboxymethyl)-10-(2'-hydroxypropyl)-1,4,7,10-tetraazocyclodecane, 1,4,7-triazacyclonane-N,N',N''-triacetic acid, 1,4,8,11-tetraazacyclotetra-decane-N,N',N'',N'''-tetraacetic acid; diethylenetriamine-pentaacetic acid (DTPA), ethylenedicysteine, bis(aminoethanethiol)carboxylic acid, triethylenetetraamine-hexaacetic acid, and 1,2-diaminocyclohexane-N,N,N',N'-tetraacetic acid.

In a further embodiment, the excipient may be a flavoring agent. Flavoring agents may be chosen from synthetic flavor oils and flavoring aromatics and/or natural oils, extracts from plants, leaves, flowers, fruits, and combinations thereof.

In still another embodiment, the excipient may be a coloring agent. Suitable color additives include food, drug and cosmetic colors (FD&C), drug and cosmetic colors (D&C), or external drug and cosmetic colors (Ext. D&C).

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

The amount of the one or more additional excipients in the pharmaceutical solid dosage form can and will vary depending upon the identity of the excipient and the identities and amounts of the other components of the pharmaceutical composition.

(viii) Optional Film Coating

In some embodiments, the pharmaceutical solid dosage form may further comprise an optional film coating. Typically, the film coating comprises at least one hydrophilic polymer and the coating does not affect the immediate release or tamper resistant properties of the pharmaceutical solid dosage form. The film coating may provide moisture protection, enhanced appearance, increased mechanical integrity, improved swallowability, improved taste, and/or masking of odors.

Film coatings are well known in the art, e.g., they are commercially available under the tradename OPADRY®. Typically, a film coating comprises at least one hydrophilic polymer and at least one plasticizer. Non-limiting examples of suitable polymers include hydroxypropylmethy cellulose, hydroxypropyl cellulose, hydroxypropyl ethylcellulose, ethylcellulose, methylcellulose, cellulose acetate phthalate, microcrystalline cellulose and carrageenan, acrylic polymers, polyvinyl alcohol, anionic and cationic polymers of methacrylic acid, copolymers of methacrylates, copolymers of acrylates and methacrylates, copolymers of ethacrylate and methylmethacrylate, polyvinylacetate phthalate, and shellac. Examples of suitable plasticizers include, without limit, triethyl citrate (TEC), acetyltriethyl citrate (ATEC), acetyl tri-n-butyl citrate (ATBC), dibutyl sebacate, diethyl phthalate, and triacetin. The film coating may optionally comprise additional agents such as a coloring agent, a filler, a flavoring agent, a taste-masking agent, a surfactant, an anti-tacking agent, and/or an anti-foaming agent. Suitable examples of these agents are well known in the art and/or are detailed above.

(ix) Exemplary Embodiments

In exemplary embodiments, the pharmaceutical solid dosage form is a tablet. The mass of the tablet may range from about 300 mg to about 600 mg or from about 400 mg to about 500 mg. The tablet may have a width ranging from about 0.2 inch to about 0.4 inch and a length ranging from about 0.45 inch to about 0.75 inch. In one exemplary embodiment, the tablet may have a single centrally-located score on the upper surface that is parallel to the short axis of the tablet. In another exemplary embodiment, the tablet may have a centrally-located score on each of the upper and lower surfaces, with each score being parallel to the short axis of the tablet. The tablet may comprise from about 20% to about 40% by weight of a hydrophilic polymer having an average molecular weight of no more than about 250,000 Da chosen from polyethylene oxide, hydroxypropyl methylcellulose, sodium carboxymethylcellulose, polyethylene glycol, a Poloxamer, and combinations thereof; about 2% to about 10% by weight of a hydrophilic polymer having an average molecular weight of at least about 400,000 Da chosen from polyethylene oxide, xanthan gum, hydroxypropyl cellulose, hydroxypropyl methylcellulose, and combinations thereof; about 50% to about 70% by weight of an effervescent system comprising an acid component and a base component; and an API chosen from oxycodone, oxymorphone, hydrocodone, hydromorphone, codeine, and morphine. The tablet may further comprise a film coating.

(c) In Vitro Release Properties

The pharmaceutical solid dosage form disclosed herein is formulated such that the API in the composition is released rapidly. Thus, the composition is termed an immediate release pharmaceutical composition. As used herein, "immediate release" generally refers to an average release of at least 70% of the API within 45 minutes in water. Unlike many immediate release compositions, the pharmaceutical solid dosage form disclosed herein comprises a blend of high molecular weight and low molecular weight hydrophilic polymers. The disclosed composition, however, also comprises an effervescent system that facilitates dissolution and rapid release of the API.

The in vitro dissolution of the API from the solid dosage form disclosed herein may be measured using an approved USP procedure. For example, dissolution may be measured using an USP approved Type 2 paddle apparatus, at a paddle speed of 50 rpm or 100 rpm, and a constant temperature of 37±0.5° C. The dissolution test may be performed in the presence of 500 mL, 900 mL, or 1,000 mL of a suitable dissolution medium (e.g., having a pH from 1.0 to 6.8). Non-limiting examples of suitable dissolution media include water, phosphate buffer (pH 6.8), acetate buffer (pH 4.5), and 0.1N HCl.

The pharmaceutical solid dosage forms disclosed herein provide immediate release of the API. In some embodiments, the pharmaceutical solid dosage form may have an average release of about 50%, 55%, 60%, 65%, 70%, 75%, 80%, 85%, 90%, 95%, or 99% of the API within 45 minutes in water. In other embodiments, the pharmaceutical solid dosage form may have an average release of about 50%, 55%, 60%, 65%, 70%, 75%, 80%, 85%, 90%, 95%, or 99% of the API within 30 minutes in water.

(d) Abuse Deterrent Properties

The pharmaceutical solid dosage forms disclosed herein also have abuse deterrent features. The blend of hydrophilic polymers and the effervescent system imparts sufficient mechanical integrity (i.e., strength, hardness, etc.) to the solid dosage form such that it is resistant to crushing, grinding, cutting, or pulverizing to form a powder comprising small particles. Additionally, because some of the hydrophilic polymers of the composition are gelling polymers, contact with a small volume of a suitable solvent leads to the formation of a viscous mixture or gel.

The mechanical integrity of the pharmaceutical solid dosage may be assessed by measuring the hardness or crushing strength of the solid dosage form. Hardness of the solid dosage form may be measured using any of numerous hardness testers, which are well known in the art. In general, the solid dosage composition has a hardness or crushing strength of at least 10 kilopond (kp). In various embodiments, the solid dosage composition may have a hardness or crushing strength ranging from about 10 kp to about 20 kp, from about 20 kp to about 30 kp, from about 30 kp to about 40 kp, or more than about 40 kp. In certain embodiments, the hardness or crushing strength of solid dosage composition is less than about 50 kp.

The mechanical integrity of the solid dosage form also may be assessed by measuring the particle size distribution after crushing, grinding, or pulverizing the composition in a suitable apparatus for a specified period of time. In some embodiments, intact solid dosage form(s) or portions thereof (e.g., generated via manual or mechanical cutting means including using a razor blade, knife, scissors, tablet splitter, hammer, mallet, mortar & pestle, pliers, locking pliers, vise grip, or other commonly available devices) may be ground or milled in a coffee grinder, a spice grinder, a nut grinder, a coffee mill, a blender, a high-shear mill, a ball mill, a co-mill, a pill crusher, a tablet grinder, or another grinding/milling apparatus. The grinding/milling time (i.e., the total time the apparatus is actively milling/grinding) may vary. In various embodiments, the grinding/milling time may be at least 3 minutes, at least 6 minutes, at least 12 minutes, at least 15 minutes, at least 20 minutes, at least 30 minutes, at least 45 minutes, or at least 60 minutes. The grinding/milling time may be continuous, or it may be intermittent. Upon grinding/milling of the solid dosage form, a fine powder fails to form. Rather, because of the mechanical integrity of the solid dosage form, grinding/milling of the solid dosage form or portions thereof produces a plurality of particles. In various embodiments, at least about 5%, at least about 10%, at least about 20%, at least about 30%, at least about 50%, or at least about 70% of the particles have average diameters of at least about 250 microns. Because the pharmaceutical solid dosage form disclosed herein is resistant to forming a fine powder by crushing, grinding or pulverizing, it deters abuse by inhalation.

Additionally, the pharmaceutical solid dosage form disclosed herein, whether whole, flattened, broken, crushed, or pulverized, forms a viscous mixture or gel when mixed with a small volume of a suitable solvent. The volume may be about 3 mL, 5 mL, or 10 mL. Suitable solvents include water, alcohols such as ethanol, acids such as acetic acid, fruit juice, and mixtures of any of the foregoing. The viscosity of the gel prevents the material from being drawn through an injection syringe needle. Consequently, the pharmaceutical solid dosage forms disclosed herein are resistant to abuse by extraction, filtering, and/or injection.

(II) Processes for Preparing Scored Solid Dosage Forms

Another aspect of the disclosure encompasses processes for preparing the solid dosage forms comprising at least one score. The processes comprise: (a) forming a mixture comprising at least one low molecular weight hydrophilic polymer, at least one high molecular weight hydrophilic polymer, and an effervescent system; (b) forming the mixture into a scored solid dosage unit; and (c) heating the scored solid dosage unit to form the scored solid dosage form. The scored solid dosage form optionally may be coated with a film coating.

(a) Forming a Mixture

The first step of the process comprises forming a mixture comprising the components of the solid dosage form, which are detailed above in section (I)(b). In general, the mixture comprises at least one API, at least one hydrophilic polymer having an average molecular weight of no more than about 250,000 Da, at least one hydrophilic polymer having an average molecular weight of at least about 400,000 Da, an effervescent system comprising an acid component and a base component, and a lubricant. The components may be combined in any order or may be premixed in various combinations before being combined together. For example, in one embodiment the acid component of the effervescent system may be co-processed with a polyalkylene glycol or Poloxamer prior to being mixed with the rest of the components. In another embodiment, the API may be combined with some of the components before being combined with the rest of the components. Thus, a variety of ordered mixing schemes are possible.

The mixture comprising the components of the pharmaceutical composition may be formed by mixing, roller mixing, drum mixing, shear mixing, dry blending, chopping, milling, roller milling, granulating, dry granulating (e.g., slugging or roller compacting), wet granulating (e.g., fluid bed granulating, high shear granulating), and other mixing techniques known in the art.

(b) Forming a Scored Solid Dosage Unit

The process further comprises forming the mixture from step (a) into a scored solid dosage unit. The score or scores can be affixed to the solid dosage unit by selecting the appropriate dies and/or punches. Means of forming solid dosage units are well known in the art. See, e.g., Gennaro, A. R., editor. "Remington: The Science & Practice of Pharmacy", 21st ed., Williams & Williams, and in the "Physician's Desk Reference", 2006, Thomson Healthcare. Suitable solid dosage units are described above in section (I)(a). In general, the solid dosage form is formulated for oral administration.

(c) Heating the Scored Solid Dosage Unit

The process further comprises heating the scored solid dosage unit. This heating step dries and cures the scored solid dosage form, wherein the cured solid dosage form may have improved properties or characteristics relative to an uncured solid dosage form. For example, the heating step may remove water from the solid dosage form, thereby protecting the effervescent system from premature effervescence. Additionally, the heating step may plasticize some of the polymers, thereby leading to increased resistance to crushing/pulverization and to more rapid release of the API.

In general, the heating step occurs at a temperature of less than about 90° C. In various embodiments, the scored solid dosage unit may be heated at a temperature from about 30° C. to about 35° C., from about 35° C. to about 40° C., from about 40° C. to about 45° C., from about 45° C. to about 50° C., from about 50° C. to about 55° C., from about 55° C. to about 60° C., from about 60° C. to about 65° C., from about 65° C. to about 70° C., from about 70° C. to about 75° C., from about 75° C. to about 80° C., from about 80° C. to about 85° C., or from about 85° C. to about 90° C. In exemplary embodiments, the heating temperature may range from about 50° C. to about 80° C.

The duration of the heating step can and will vary depending upon the components of the solid dosage form and the heating temperature. The duration of the heating step may range from about 10 minutes to about 10 hours. In general, the higher the temperature, the shorter the duration of time for the heating step. In an exemplary embodiment, the tablet may be heated to a temperature from about 65° C. to about 75° C. for a period of time ranging from about 1 hour to about 2 hours.

(d) Optionally Coating the Scored Solid Dosage Form

The scored solid dosage form may be coated with a film coating. Suitable film coatings are detailed above in section (I)(b)(viii).

DEFINITIONS

When introducing components of the embodiments described herein, the articles "a", "an", "the" and "said" are intended to mean that there are one or more of the elements. The terms "comprising", "including" and "having" are intended to be inclusive and mean that there may be additional components other than the listed components.

If the components described herein have asymmetric centers, all chiral, diastereomeric, racemic forms and all geometric isomeric forms of a structure are intended, unless the specific stereochemistry or isomeric form is specifically indicated.

Having described the invention in detail, it will be apparent that modifications and variations are possible without departing from the scope of the invention defined in the appended claims.

EXAMPLES

The following examples are included to illustrate, but not to limit the claimed pharmaceutical compositions and processes for making.

Example 1

Abuse Deterrent Round Tablet Scored on One Surface

Table 1 details the immediate release, abuse deterrent formulation used in this example. The tartaric acid was co-processed with Kolliphor P407 by mixing in a high-shear granulator during which the temperature was raised to 65° C. The ratio of the tartaric acid to Kolliphor was 18.1:1.0 (w/w). After the hot-melt process was complete, the bowl was cooled to room temperature and sieved through a 20 Mesh sieve screen. The material going through the screen was mixed with the rest of the tablet components using a V-blender. Round tablets were prepared using a rotary tablet press. The tablets were 0.3740 inch in diameter, with a score line on one surface of the tablet. The tablets were cured at 70-75° C. in a pan coater, and then coated with Opadry coating materials marketed by Colorcon, Inc. The weights of an intact tablet before and after coating were 425 mg and 443 mg, respectively.

TABLE 1

Tablet Composition.

| Component | Mg/tab | % wt |
|---|---|---|
| Oxycodone HCl | 15.0 | 3.53 |
| Tartaric acid co-processed with Kolliphor P407 | 127.4 | 29.98 |
| EfferSoda ®12 | 142.6 | 33.55 |
| Polyox N10 LEO (100K) | 52.7 | 12.40 |
| Polyox WSR 301 NF LEO (4 Million) | 15.0 | 3.53 |
| Carboxymethylcellulose, sodium | 20.0 | 4.71 |
| Hydroxypropyl methylcellulose, Coarse | 30.0 | 7.06 |
| Xanthan gum | 10.6 | 2.49 |
| Micronized Talc | 10.1 | 2.38 |
| Magnesium stearate | 1.6 | 0.38 |
| Total | 425.0 | 100.01 |

The tablets were evaluated using the guidelines and criteria set forth by the FDA (Draft Guidance for Industry Tablet Scoring: Nomenclature, Labeling, and Data for Evaluation, CDER, FDA, August, 2011). The tablets were split manually or mechanically using a tablet splitter. Weight loss was determined by determining the combined weight of 20 tablets, the combined weight of 40 manually split, de-dusted halves, and the combined weight of 40 mechanically split, de-dusted halves. If the weight loss after splitting was <3.0%, then the tablet passed the splitting test. Friability was determined using the USP friability test (100 revolutions) with 40 manually or mechanically split tablet halves. Tablet weight was measured before and after the test, and friability is expressed as a percentage loss of the pretest weight. The USP friability requirement is 1.0% (or less).

The round tablets prepared above could not be broken manually but could be broken using a tablet splitter. The weight loss of the mechanically split tablets was 0.20%. The friability score for the mechanically split tablets was 0.06%. No content uniformity or dissolution data were collected on the broken tablets. These data indicate that the score in the round abuse deterrent oxycodone HCl tablets did not meet all the criteria set forth in the FDA guidelines referenced above.

Example 2

Abuse Deterrent Oval Tablet Scored on One Surface

Figure 2:
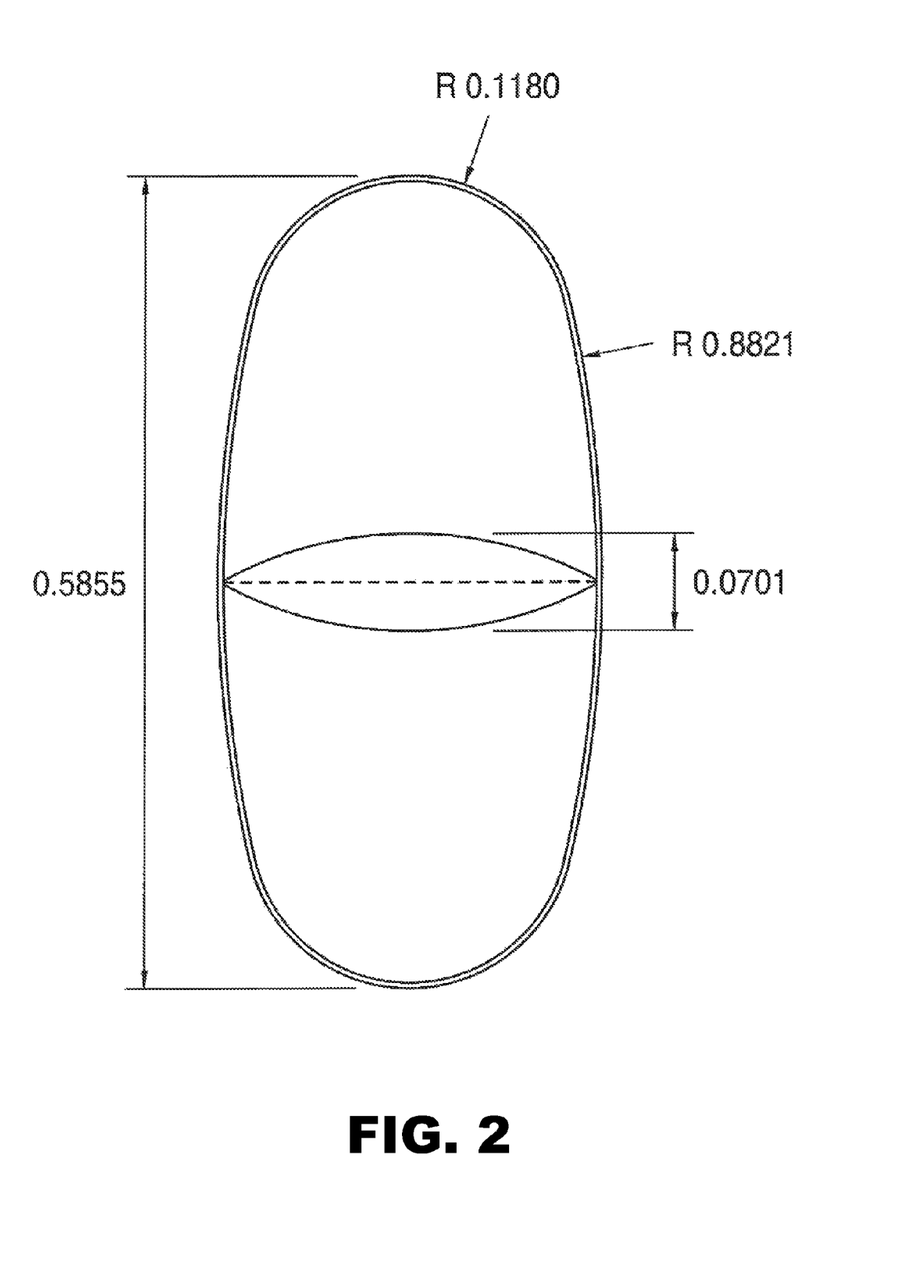
FIG. 2 shows a face view of an oval tablet with a C type score.

Tablets were prepared as described in Example 1, except the tablets were oval in shape (width=0.2559 inch and length=0.5512 inch) with a score on one surface (see FIG. 1A and FIG. 2). The tablets were cured and coated before testing. The weight of an intact coated tablet was 441 mg.

Weight loss and friability were determined as described above in Example 1. Table 2 presents the data for manually split and mechanically split tablets. The tablet met the weight loss and friability standards.

TABLE 2

Weight loss and friability data.

| | Split manually | Split mechanically |
|---|---|---|
| Weight loss test | | |
| Weight of 20 tablets prior to splitting | 8.837 g | 8.824 |
| Cumulative weight of 40 halves | 8.835 g | 8.813 |
| % Weight loss post-splitting | 0.01% | 0.13% |
| Result | Meets criteria | Meets criteria |
| Friability test | | |
| % Friability (100 revolutions) | 0.02% | 0.09% |
| Result | Meets criteria | Meets criteria |

The content uniformity refers to the degree of uniformity in the amount of the active ingredient among dosage units. The amount of oxycodone hydrochloride was determined in intact tablets and split tablet halves using an HPLC method. The USP specification for these tablets is an Acceptance Value (AV) of 15.0 or less (Level 1). As shown in Table 3, the tablet met the Level 1 standard.

TABLE 3

Content uniformity data.

| | Oxycodone hydrochloride content (% claim) | | |
|---|---|---|---|
| Sample | Intact tablets | Split manually | Split mechanically |
| Average (N = 10) | 98.32 | 99.62 | 100.05 |
| Std. Dev. | 1.54 | 3.24 | 5.38 |
| % RSD | 1.57 | 3.25 | 5.38 |
| Minimum | 95.03 | 95.43 | 92.87 |
| Maximum | 100.47 | 106.43 | 106.96 |
| Acceptance value | 3.9 | 7.8 | 12.9 |
| Result | Passes in Level 1 | Passes in Level 1 | Passes in Level 1 |

Intact tablets, manually split tablet halves, and mechanically split tablet halves were tested for in vitro dissolution of oxycodone hydrochloride. Dissolution was determined using USP Apparatus Type 2, Paddles, 50 rpm, 37±0.5° C., in 500 mL water. Oxycodone content was determined in the dissolution medium after 45 minutes using an HPLC method. Table 4 presents the dissolution data. The tablet met the specification standard that at least 70% of the active ingredient is released within 45 minutes (Level 1).

TABLE 4

Dissolution data.

| | Oxycodone hydrochloride dissolved (% claim) | | |
|---|---|---|---|
| Sample | Intact tablets | Split manually | Split mechanically |
| Average | 101.7 | 98.4 | 102.7 |
| Std. Dev. | 1.1 | 3.8 | 4.4 |
| % RSD | 1.1 | 3.9 | 4.3 |
| Minimum | 100.3 | 94.4 | 97.2 |
| Maximum | 102.8 | 105.1 | 109.5 |
| N | 6 | 12 | 12 |
| Result | Passes in Level 1 | Passes in Level 1 | Passes in Level 1 |

The tablets prepared in this example met the FDA guidelines, indicating that the score was functional in these oval-shaped abuse deterrent tablets.

Example 3

Abuse Deterrent Oval Tablet Scored on Two Surfaces

Tablets were prepared using the formulation presented in Table 5. The tartaric acid and Kolliphor were used as received without co-processing, and the components were processed essentially as described above in Example 1. Oval tablets were prepared (width=0.2765 inch and length=0.5865 inch) and scored on the upper and lower surfaces. See FIG. 1B. The tablets were cured for 2 hours at 70-75° C. and coated as described above. The weight of an intact coated tablet was 474 mg.

TABLE 5

Tablet Composition.

| Component | Mg/tablet after adjustment | Wt. % after adjustment |
|---|---|---|
| Oxycodone HCl | 5.0 | 1.09 |
| L-(+)-Tartaric Acid | 125.8 | 27.35 |
| PEG 3350 | 2.9 | 0.63 |
| Effersoda ®12 | 148.5 | 32.28 |
| Polyox N10 LEO (100K) | 100.6 | 21.87 |
| Polyox WSR 301 NF LEO | 14.7 | 3.20 |
| Na. CMC (30000)-Walocel | 20.0 | 4.35 |
| Methocel K100M CR | 30.0 | 6.52 |
| Xanthan Gum - Vanzan (NF) | 10.6 | 2.30 |
| Magnesium stearate | 1.9 | 0.41 |
| Total | 460.0 | 100.00 |

Weight was determined by weighing 62 intact tablets. Twenty tablets were split using a tablet cutter (mechanical splitting) and each half was weighed. Twenty tablets were manually broken and their weights recorded. Summary of data is given in Table 6. The average weight of intact tablets was 473.79 mg, so the theoretical weight of each half was 236.90 mg (473.79/2=236.90). For the manually split tablets, the average weight was 237.25 mg. When expressed as percent of theory, the average weight of the half tablet was 100.1% (237.25×100/236.90=100.1%).

TABLE 6

Weight data.

| | Intact | Split manually | | Split mechanically | |
|---|---|---|---|---|---|
| | In mg | In mg | In % of theory | In mg | In % of theory |
| Average | 473.79 | 237.25 | 100.1 | 237.41 | 100.2 |
| SD | 6.96 | 4.27 | 1.8 | 4.21 | 1.8 |
| RSD | 1.47% | 1.80% | 1.8% | 1.78% | 1.8% |
| Minimum | 460.34 | 229.35 | 96.8 | 228.43 | 96.4 |
| Maximum | 487.85 | 249.00 | 105.1 | 245.29 | 103.5 |
| N | 62 | 40 | 40 | 40 | 40 |

Weight loss and friability were determined as described above in Example 1. Table 7 presents the data for manually split and mechanically split tablets.

TABLE 7

Weight loss and friability data.

| | Split manually | Split mechanically |
|---|---|---|
| Weight loss test | | |
| Weight of 20 tablets prior to splitting | 9.518 g | 9.460 g |
| Weight of 40 broken tablets | 9.480 g | 9.454 g |
| % Weight loss post-splitting | 0.40% | 0.06% |
| Result | Meets criteria | Meets criteria |
| Friability test | | |
| % Friability (100 revolutions) | 0.02% | 0.01% |
| Result | Meets criteria | Meets criteria |

Content uniformity was measured as described above in Example 2, and the data are presented in Table 8. The tablet passed Level 1 standards.

TABLE 8

Content Uniformity.

| | Oxycodone hydrochloride content (% claim) | | |
|---|---|---|---|
| Sample | Intact tablets | Split manually | Split mechanically |
| Average (N = 10) | 103.1 | 99.8 | 104.0 |
| Std. Dev. | 2.1 | 1.8 | 2.3 |
| % RSD | 2.0% | 1.8% | 2.2% |
| Minimum | 100.2 | 96.1 | 100.0 |
| Maximum | 106.8 | 102.0 | 107.0 |
| Acceptance value | 6.55 | 4.24 | 7.88 |
| Result | Passes in Level 1 | Passes in Level 1 | Passes in Level 1 |

The dissolution test was performed on intact, manually split, and mechanically split tablets essentially as detailed above in Example 2. The data are shown in Table 9. The tablet met the Level 1 standard.

TABLE 9

Dissolution Data.

| | Oxycodone hydrochloride dissolved (% claim) | | |
|---|---|---|---|
| Sample | Intact tablets | Split manually | Split mechanically |
| Average (N = 12) | 97.54 | 97.16 | 96.54 |
| Std. Dev. | 3.20049 | 1.87362 | 3.52261 |
| % RSD | 3.28 | 1.93 | 3.65 |

TABLE 9-continued

Dissolution Data.

| | Oxycodone hydrochloride dissolved (% claim) | | |
|---|---|---|---|
| Sample | Intact tablets | Split manually | Split mechanically |
| Minimum | 90.6 | 94.6 | 91.6 |
| Maximum | 102.1 | 100.6 | 104.2 |
| Result | Passes in Level 1 | Passes in Level 1 | Passes in Level 1 |

This example showed that the score was functional in this oval-shaped abuse deterrent tablet.

What is claimed is:

1. A pharmaceutical solid dosage form comprising at least one active pharmaceutical ingredient (API) or a pharmaceutically acceptable salt thereof, at least one low molecular weight hydrophilic polymer, at least one high molecular weight hydrophilic polymer, and an effervescent system, wherein the solid dosage form comprises at least one score, provides immediate release of the API, and breaks into a plurality of particles having an average diameter of greater than about 250 microns rather than a fine powder when crushed, ground, or pulverized, and wherein contact with a suitable solvent leads to formation of a viscous gel.

2. The pharmaceutical solid dosage form of claim 1, wherein the score is a functional score.

3. The pharmaceutical solid dosage form of claim 1, wherein the solid dosage form has one score, with the score on either an upper surface or a lower surface.

4. The pharmaceutical solid dosage form of claim 1, wherein the solid dosage form has two scores, with a first score on an upper surface and a second score on a lower surface.

5. The pharmaceutical solid dosage form of claim 1, wherein the solid dosage form is a tablet, optionally having an oval shape.

6. The pharmaceutical solid dosage form of claim 1, wherein the solid dosage form further comprises a film coating.

7. The pharmaceutical solid dosage form of claim 1, wherein, upon splitting the solid dosage form to yield split solid dosage portions, the split solid dosage portions have a loss of mass of less than about 3.0% and a friability of no more than about 1.0%.

8. The pharmaceutical solid dosage form of claim 7, wherein the split solid dosage portions have an in vitro dissolution rate of at least about 70% of the API within 45 minutes when measured using an USP approved procedure.

9. The pharmaceutical solid dosage form of claim 7, wherein the split solid dosage portions have an in vitro dissolution rate of at least about 80% of the API within 30 minutes when measured using an USP approved procedure.

10. The pharmaceutical solid dosage form of claim 1, wherein the API is an opioid or a combination of an opioid and a non-opioid analgesic.

11. The pharmaceutical solid dosage form of claim 10, wherein the opioid is oxycodone, oxymorphone, hydrocodone, hydromorphone, codeine, or morphine.

12. The pharmaceutical solid dosage form of claim 1, wherein the low molecular weight hydrophilic polymer has an average molecular weight of no more than about 250,000 Daltons; the low molecular weight hydrophilic polymer is polyethylene oxide, hydroxypropyl methylcellulose, sodium carboxymethylcellulose, polyethylene glycol, a Poloxamer, or a combination thereof; and the low molecular weight hydrophilic polymer is present in an amount from about 5% to about 50% by weight of the solid dosage form.

13. The pharmaceutical solid dosage form of claim 1, wherein the high molecular weight hydrophilic polymer has an average molecular weight of at least about 400,000; the high molecular weight hydrophilic polymer is polyethylene oxide, hydroxypropyl cellulose, hydroxypropyl methylcellulose, xanthan gum, or a combination thereof; and the high molecular weight hydrophilic polymer is present in an amount from about 0.1% to about 30% by weight of the solid dosage form.

14. The pharmaceutical solid dosage form of claim 1, wherein the effervescent system comprises an acid component and a base component; the acid component is an organic acid, an inorganic acid, or a combination thereof; the base component is an alkali metal bicarbonate, an alkaline earth metal bicarbonate, an alkali metal carbonate, an organic carbonate, or a combination thereof; and the effervescent system is present in an amount from about 20% to about 90% by weight of solid dosage form.

15. The pharmaceutical solid dosage form of claim 1, wherein the solid dosage form is a tablet; the low molecular weight hydrophilic polymer has an average molecular weight of no more than about 250,000 Da and is present in an amount from about 20% to about 40% by weight of the solid dosage form; the high molecular weight hydrophilic polymer has an average molecular weight of at least about 400,000 Da and is present in an amount from about 2% to about 10% by weight of the solid dosage form; the effervescent system comprises an acid component and a base component and is present in an amount from about 50% to about 70% by weight of the solid dosage form; and the API is oxycodone, oxymorphone, hydrocodone, hydromorphone, codeine, or morphine.

16. The pharmaceutical solid dosage form of claim 15, wherein the low molecular weight hydrophilic polymer is polyethylene oxide, hydroxypropyl methylcellulose, sodium carboxymethylcellulose, polyethylene glycol, a Poloxamer, or a combination thereof; the high molecular weight hydrophilic polymer is polyethylene oxide, hydroxypropyl cellulose, hydroxypropyl methylcellulose, xanthan gum, or a combination thereof; the acid component of the effervescent system is an organic acid; and the base component of the effervescent system is an alkali metal bicarbonate, an alkali metal carbonate, or a combination thereof.

17. The pharmaceutical solid dosage form of claim 16, wherein the API is oxycodone, oxymorphone, hydrocodone, hydromorphone, codeine, or morphine.

18. The pharmaceutical solid dosage form of claim 17 further comprising a film coating.

19. The pharmaceutical solid dosage form of claim 1, wherein the suitable solvent is water, an alcohol, an acid, a fruit juice, or a combination thereof.

* * * * *